United States Patent [19]

Mansfield et al.

[11] Patent Number: 5,778,047
[45] Date of Patent: Jul. 7, 1998

[54] RADIOTHERAPY COUCH TOP

[75] Inventors: Stanley Mansfield, Sunnyvale; Ross Bernald Hannibal, Saratoga, both of Calif.

[73] Assignee: Varian Associates, Inc., Palo Alto, Calif.

[21] Appl. No.: 735,902

[22] Filed: Oct. 24, 1996

[51] Int. Cl.$^6$ ............................................. A61B 6/04
[52] U.S. Cl. ......................... 378/209; 378/208; 378/177; 378/179
[58] Field of Search .................... 378/208, 209, 378/65, 64, 68, 177, 179; 5/600

[56] References Cited

U.S. PATENT DOCUMENTS

| | | | |
|---|---|---|---|
| 4,575,064 | 3/1986 | Menor | 378/209 |
| 5,537,454 | 7/1996 | Korver, II | 378/65 |

*Primary Examiner*—Don Wong
*Attorney, Agent, or Firm*—Hunter L. Auvang

[57] ABSTRACT

A radiotherapy couch top has a frame and preferably a pair of beams extending parallel to each other, capable independently of moving towards or away from each other while keeping their mutually parallel longitudinal direction. For supporting the beams in this way, at least two linear slide bearing ways are provided, extending parallel to each other in a transverse direction perpendicular to the beams, at least one of them being supported by the frame. A pair of riding blocks are on each of these linear slide bearing ways, each supporting a corresponding one of the beams and slidable along the linear slide bearing way. Panels are placed over the beams, including one attached to the frame and another which is removable. The removable panel may be replaced with another having an open window section provided with a grid of carbon fiber stringing capable of supporting the patient and allowing projection of radiation directly onto the patient's skin.

11 Claims, 5 Drawing Sheets

RADIOTHERAPY COUCH TOP

This invention relates to the top structure of a couch which can be used to support a patient during radiotherapy treatment or simulation. More in particular, this invention relates to such a couch top structure which can be moved to avoid unwanted attenuation of radiation beam for radiotherapy treatment.

BACKGROUND OF THE INVENTION

As shown in FIG. 1, a conventional double ended metal couch top 60 has two separate sections on each end of a central pivot bearing with a vertical axis of rotation. One end forms an open window 62 with panels (not shown) supporting the patient resting on side rail beams in the main structure, permitting an unobstructed treatment beam directed from below. The other end forms a center spine structure 64. Panels for supporting the patient are cantilevered off this central structure, permitting unobstructed treatment beam directed from an oblique angle.

With a couch top thus structured, the patient must be removed from the couch in order to switch from the open window 62 to center spine construction 64 or back. When manually swinging the top to bring the opposite end into position, the operator must take care to prevent it from colliding with other parts of the machine or other objects in the room. Because of its complex shape, it is not practical to fabricate it out of carbon fiber or similar radio-transparent material. Thus, it is limited to use on treatment machines. Radiotherapy simulators must approximate the mechanical characteristics of this top using a fixed couch typically made of carbon fiber design so as not to obstruct the x-ray imaging system employed on such a machine.

Another conventional design for couch top 70, as shown in FIG. 2, utilizes two C-shaped structural connections 72 each supported by a pivot bearing with a horizontal axis of rotation. These C-shaped arms 72 can be independently swung through an arc to a position either apart or together. An extension of the horizontal couch top surface 76 is supported by these C-arms 72 through identical horizontal bearings. Panels can be supported by structure 74 at each end of the C-arms 72.

The shape of the movable C-arms 72, however, is inherently inefficient because it is internally loaded in a combination of torsion and bending. This results in higher deflection for a given load than a comparable straight beam loaded in bending. The physical size and manufacturing tolerances imposed on the horizontal pivot bearings limit their mechanical accuracy and rigidity. Both effects limit the overall mechanical stability of this type of couch top. Because the arms must swing down to change position, they may collide with parts of the machine immediately below the couch top, including an image detector or beam collimator as the couch top is retracted.

SUMMARY OF THE INVENTION

It is therefore an object of this invention to provide an improved radiotherapy couch top which is mechanically rigid and stable and allows rapid changes in the placement of structure with or without a patient load.

It is another object of this invention to provide such a radiotherapy couch top which will lends itself to the practical use of carbon fiber materials accommodating the needs of both radiotherapy simulation and treatment.

A radiotherapy couch top embodying this invention, with which the above and other objects can be accomplished, may be characterized as comprising a frame and a pair of beams extending parallel to each other, capable of independently moving towards or away from each other while keeping their mutually parallel longitudinal direction. For supporting the beams in this way, at least two linear slide bearing ways are provided, extending parallel to each other in a transverse direction perpendicular to the beams, at least one of them being supported by the frame. A pair of riding blocks are on each of these linear slide bearing ways, each supporting a corresponding one of the beams and slidable along the linear slide bearing way. Panels are placed over the beams, including one attached to the frame and another which is removable, having an open window section provided with a grid of fiber stringing capable of supporting the patient and allowing projection of radiation directly onto the patient's skin.

Another embodiment of the radiotherapy couch top of the present invention characterized by a frame having side members, at least one movable beam extending from said frame parallel to said side members of the frame in a longitudinal direction, at least one linear slide bearing way extending in a transverse direction perpendicular to said longitudinal direction and being connected to said frame, at least one linear bearing block affixed to said beam, said linear bearing block being adapted to slide along said linear slide bearing way to allow the beam to move in said transverse direction while remaining oriented in said longitudinal direction, a horizontally extending fixed panel affixed to said frame over said beam for supporting a patient thereon, and a horizontally extending removable panel disposed over said beam for also supporting said patient, said removable panel being supported by said frame and by a support connected to an exposed end of said beam.

BRIEF DESCRIPTION OF THE DRAWINGS

The accompanying drawings, which are incorporated in and form a part of this specification, illustrate embodiments of the invention and, together with the description, serve to explain the principles of the invention. In the drawings.

DETAILED DESCRIPTION OF THE PREFERRED EMBODIMENT

Figure 3:
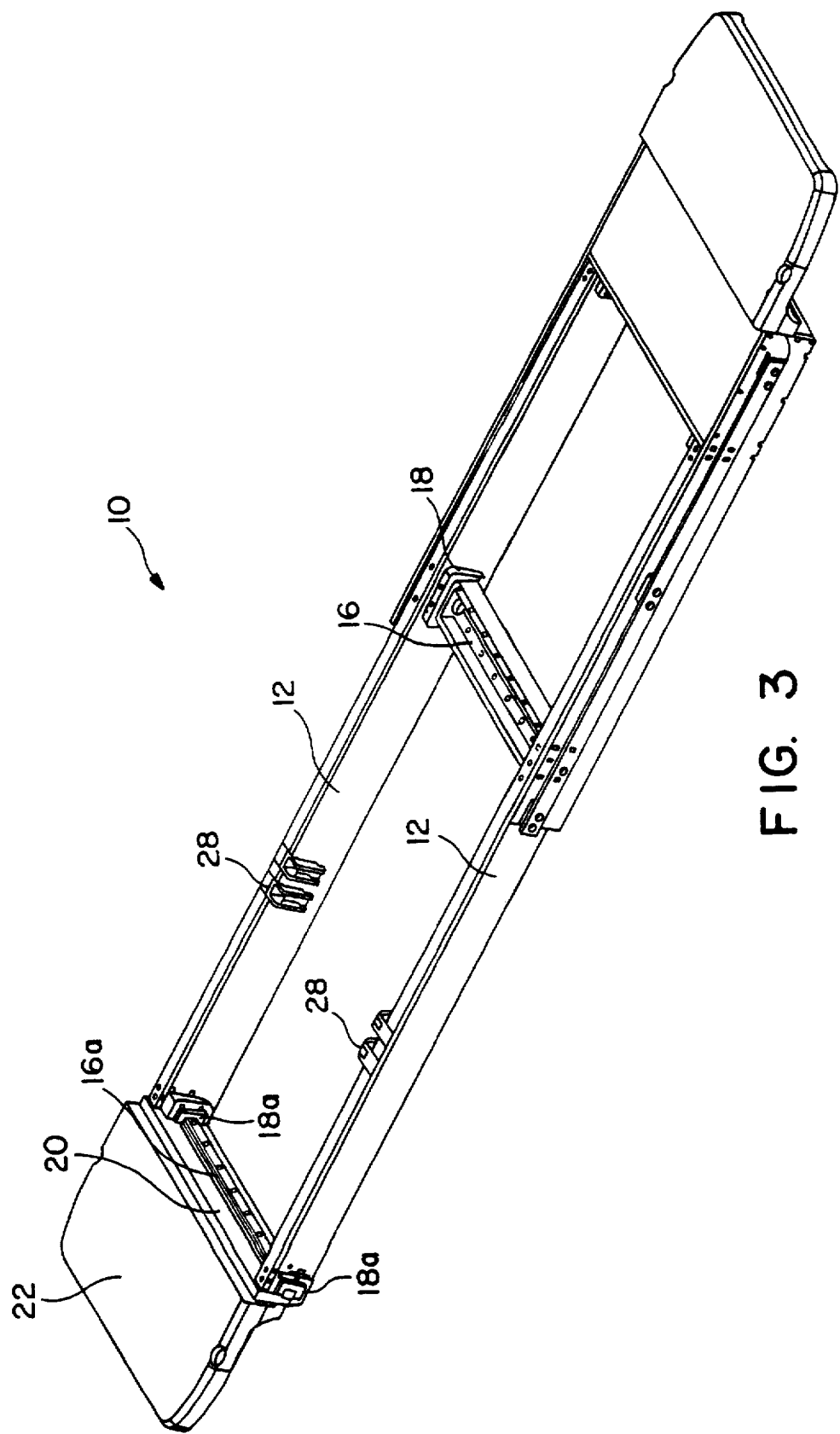
FIG. 3 is a diagonal view of a radiotherapy couch top embodying this invention with panels removed, when its two beams are at mutually separated positions.
Figure 4:
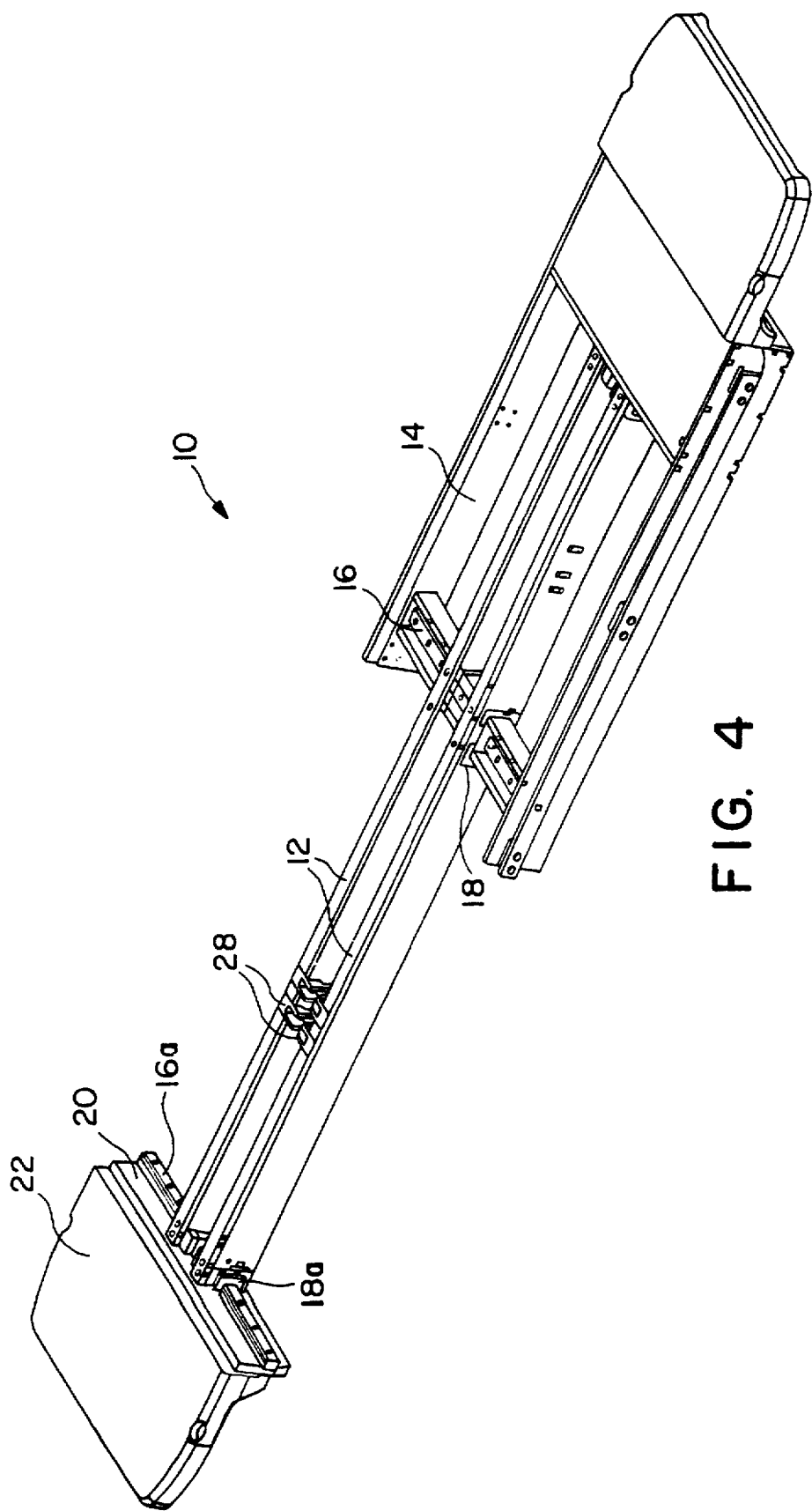
FIG. 4 is another diagonal view of the radiotherapy couch top of FIG. 3 with panels removed when its two beams are at mutually adjacent positions.

As shown in FIGS. 3 and 4, a radiotherapy couch top 10 according to this invention is most preferably characterized as having two beams 12, which are supported by a fixed frame 14 so as to be parallel to each other and movable towards or away from each other while remaining in the mutually parallel orientation relationship. The fixed frame 14 of the radiotherapy couch top 10 is mounted on a base (not shown) that is fixed and set into the floor of the treatment area. For this purpose, two linear slide bearing ways 16 (only one visible in FIGS. 3 and 4) are mounted to and supported by the fixed frame 14 so as to be both horizontal and parallel to each other. A pair of linear bearing or riding blocks 18 slidably ride on each of these linear slide bearing ways 16, each of the pair supporting a corresponding one of the beams 12 such that these linear bearing blocks 18 allow the two beams 12 to independently move transversely to the direction of their extension (that is, their longitudinal direction) while maintaining their longitudinal directions. By moving one or more of the beams during radiotherapy treatment, the support structure, i.e., the movable beam of the couch top, can be positioned so as to avoid attenuation of the radiation beam used in the treatment.

A third pair of linear slide blocks 18a is mounted at the ends of the beams 12 distal from the fixed frame 14, supporting a third linear slide bearing way 16a which is mounted to a couch extension support 20 supporting a removable extension panel 22.

It is within the scope of this invention to use a single beam, providing a suitable material of sufficient rigidity is used to construct the single beam. The use of a pair of beams is preferred, and additional beams may be used if greater stability is desired. In addition, the number of linear slide bearing ways and corresponding linear slide blocks can be varied. It is preferred that at least two linear slide bearing ways be used, with three linear slide bearing ways being most preferred. The number of linear slide bearing ways may be increased to support the moment loads created by the patient load and be able to keep the beams 12 parallel to each other. Also, the number of slide blocks will vary with the number of beams. For example, if there are three linear slide bearing ways and two beams, the present invention would employ six slide blocks.

Figure 5:
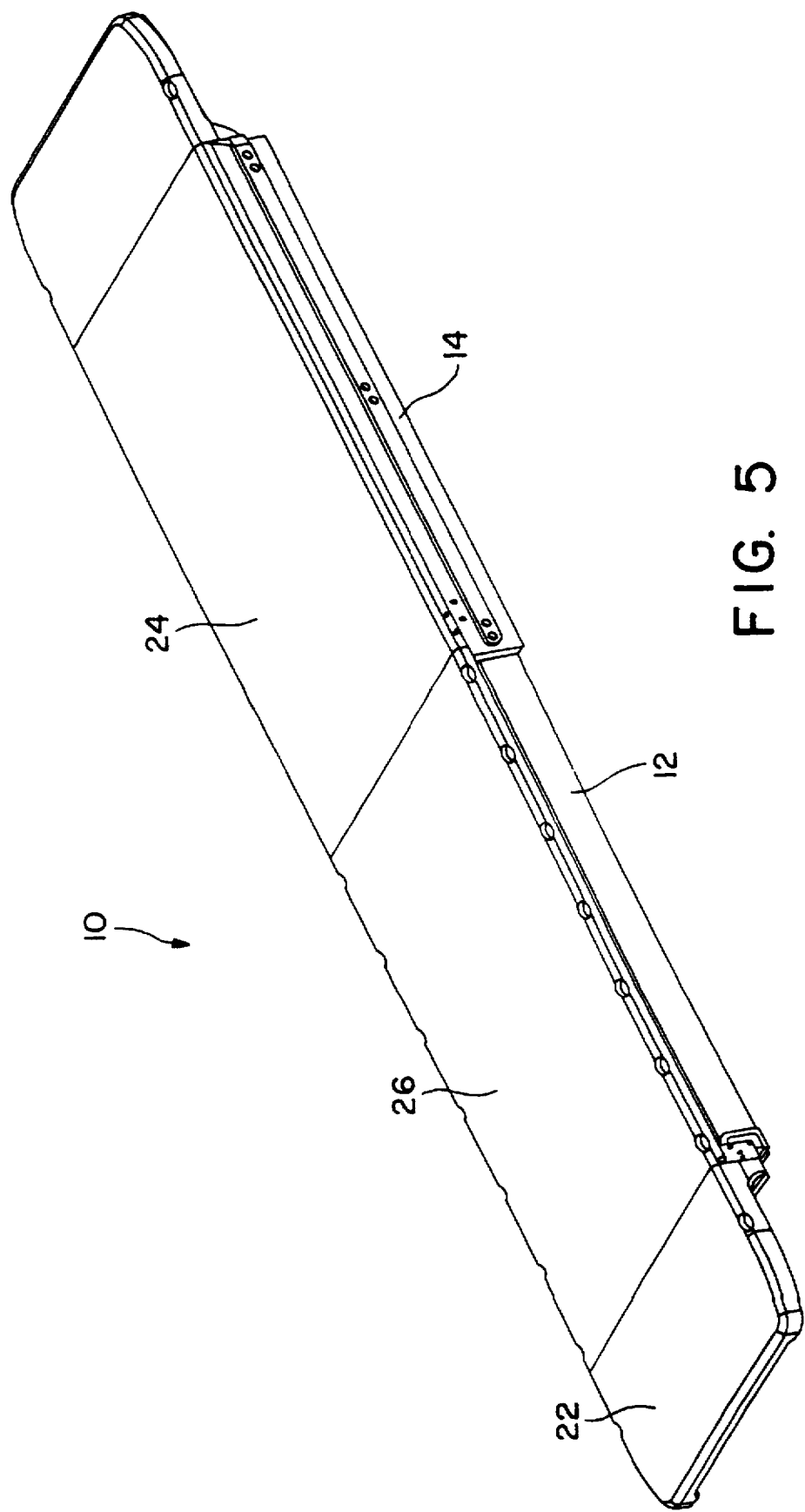
FIG. 5 is still another diagonal view of the radiotherapy couch top of FIGS. 3 and 4 with panels placed on top.

As shown in FIG. 5, a fixed flat panel 24 is mounted to the fixed frame 14, and a removable flat panel 26 can be placed in the opening between the removable extension panel 22 and the fixed flat panel 24 so as to together form a continuous flat surface to support the patient. With the couch top 10 thus structured, the removable flat panel 26 supports the bulk of the patient's load and in turn is supported by the fixed frame 14 on one end and by the couch extension support 20 on the other. Roller bearings 28 may be optionally attached to the beams 12 as shown in FIGS. 3 and 4. The roller bearing 28 serve to provide further support to the removable flat panel 26 between its two ends.

Figure 6:
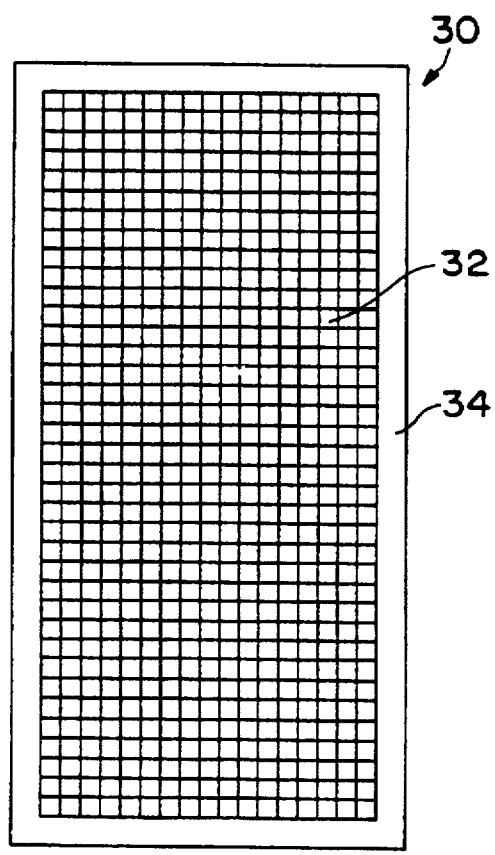
FIG. 6 is a plan view of a removable open grid panel which may replace the removable flat panel of FIG. 5.

The removable flat panel 26 can be replaced by a removable open grid panel 30, as shown in FIG. 6, having a very large posterior window 32 surrounded by a frame 34, parts of which align with the side edges of the fixed flat panel 24. The window 32 is covered with a grid of fiber stringing. The stringing can be made of natural or man-made fibers such as gut or nylon. Carbon fiber is preferred. The fiber may be interlaced in the style of a tennis racket. The removable open grid panel 30 is capable of supporting the weight of the patient while allowing projection of radiation directly onto the patient's skin surface from below.

Figure 1:
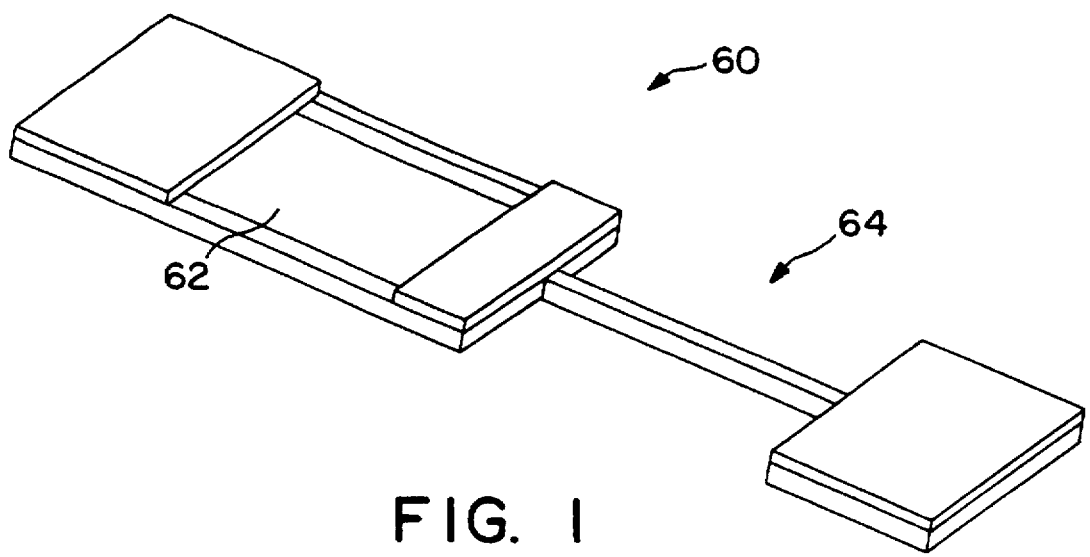
FIG. 1 is a diagonal view of a prior art double ended couch top with panels removed.
Figure 2:
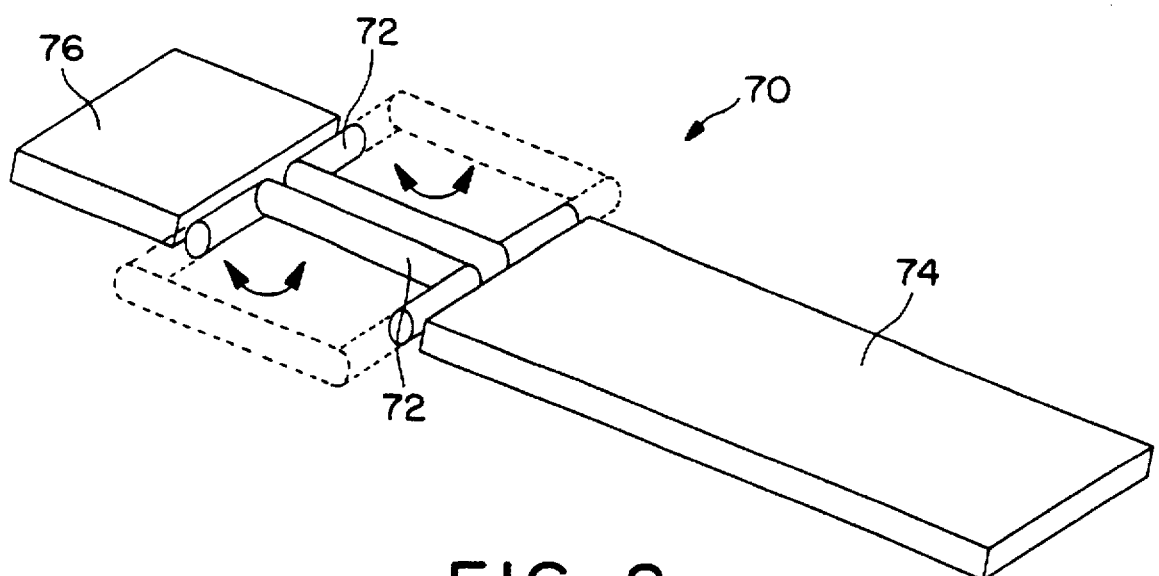
FIG. 2 is a diagonal view of a prior art C-arm couch top with panels removed.
Figure 7:
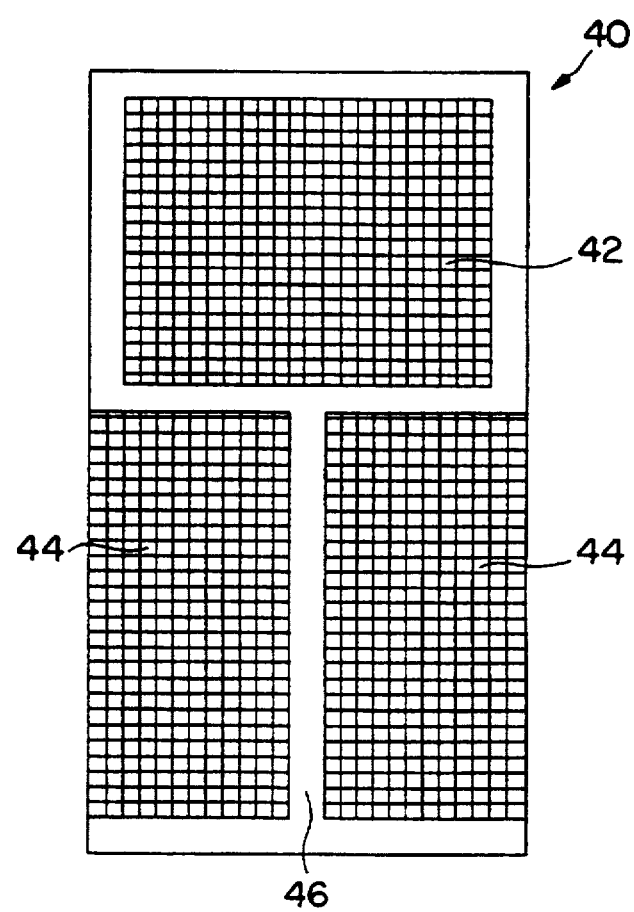
FIG. 7 is a plan view of another removable open grid panel which may replace the removable panels of FIGS. 5 and 6.

FIG. 7 shows another removable open grid panel 40 for use with the couch top 10 in place of the removable flat panel 26. The removable open grid panel 40 provides a combination of a posterior window 42 for posterior fields and tangent windows 44. There is a center frame member 46 and no side framing along the portions of the edge of the tangent window section of the removable open grid panel 40. This open grid panel is adapted for oblique fields, replacing the functionality of the side rail and center spine sections of prior art double ended couch tops shown in FIG. 1.

Figure 8:
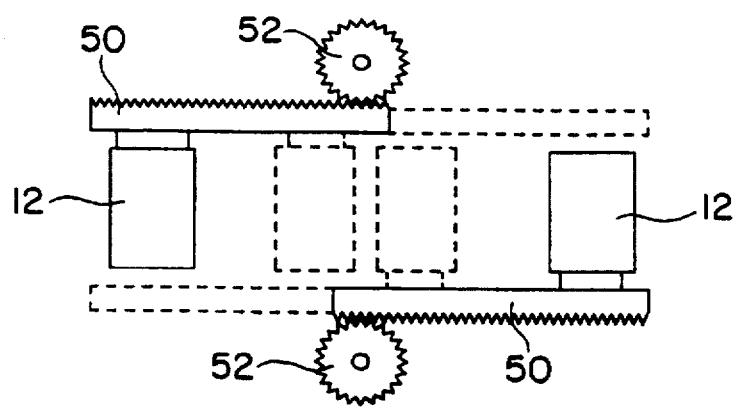
FIG. 8 is a schematic horizontal view of a mechanism for automatically moving the beams of FIGS. 3 and 4.

Although the invention has been described above primarily with reference to the most preferred embodiment as shown in the Figures. This described embodiment is not intended to limit the scope of the invention. Many modifications and variations are possible within the scope of the invention, as are partially describe above. Although the beams 12 can be moved manually towards or away from each other, for example, they may be motorized. As shown in FIG. 8, each of the beams 12 may be attached to a rack 50 in an engaging relationship with a pinion 52 attached to the drive shaft of a motor (not shown) such that they can be moved independently away from each other to mutually separated positions (as shown by solid lines) or towards each other to mutually adjacent positions (as shown by broken lines). It now goes without saying that any other motion-transmitting mechanisms can be substituted for the rack-and-pinion combination such as belts with pulleys. Such motorization will permit automation of beam placement in concert with automation of multiple static treatment fields.

Without the removable extension panel 22 in place, the couch extension support 20 may be adapted to provide mounting means for supporting various specialized attachments dedicated for head and neck treatments or stereotactic radiosurgery. Although not specifically illustrated, any and all of the panels may include means for precisely repeating the position of devices for immobilizing the patient on the couch top.

In summary, the invention allows rapid changes in the placement of structure with or without patient load. It is mechanically much more rigid and stable than prior art C-arm designs. Because it is possible to support panels all along their length, a much longer couch top and clinically usable area can be provided. Since the beams 12 can be moved independently of each other, better mechanical stability can be attained. Since the beams 12 can slide on the linear slide bearing ways, their separation can be adjusted much more easily than by cranking a handle. All modifications and variations which may be apparent to a person skilled in the art, in view of the advantages described above, are intended to be within the scope of the invention.

What is claimed is:

1. A radiotherapy couch top comprising:

a fixed frame having two side members;

a pair of movable beams extending beyond said side members of said fixed frame parallel to each other in a longitudinal direction, each of said pair of movable beams having distal and proximal ends;

a first and second linear slide bearing ways extending parallel to each other in a transverse direction perpendicular to said longitudinal direction, said first and second linear slide bearing ways being attached to said side member of said fixed frame;

pairs of riding blocks, each of said pairs of riding blocks being adapted to slide along one of said linear slide bearing ways, with one of each of said pairs of riding blocks being affixed to one of said beams, the other of each of said pairs of riding blocks being affixed to the other of said beams such that each of said beams can move in said transverse direction independently while remaining oriented in said longitudinal direction, a first of said pairs of riding blocks located near the proximal ends of said pair of movable beams slidably attached to said first linear slide bearing way;

a horizontally extending fixed panel affixed to said frame over said beams for supporting a patient thereon; and a horizontally extending removable panel disposed over said beams and adjacent to said fixed panel for also supporting said patient thereon.

2. The radiotherapy couch top of claim 1 further comprising an open grid panel adapted to replace said removable panel disposed over said beams, said open grid panel having open grid surface areas which permit transmission therethrough of radiation for radiotherapy.

3. The radiotherapy couch top of claim 2 wherein said open grid panel comprises a grid of carbon fiber and is capable of supporting said patient thereon.

4. The radiotherapy couch top of claim 2 wherein said open grid surface areas include a central area surrounded by a frame.

5. The radiotherapy couch top of claim 2 wherein said open grid surface areas include a grid area surrounded by a frame and two peripheral grid areas supported by a center frame member and unsupported on the side edges of said open grid panel.

6. The radiotherapy couch top of claim 1 further comprising an extension panel attached to a third linear slide bearing way slidably attached to a second of said pairs of riding blocks located near the distal end of said pair of movable beams, said removable panel being disposable between said fixed panel and said extension panel.

7. The radiotherapy couch top of claim 6 wherein said extension panel is removable from said third linear slide bearing way.

8. The radiotherapy couch top of claim 1 further comprising a motor means for automatically and independently moving said beams in said transverse direction.

9. The radiotherapy couch top of claim 1 wherein said beams are movable manually in said transverse direction.

10. The radiotherapy couch top of claim 1 wherein a roller bearing is attached to said beams to provide additional support for said removable panel.

11. A method for radiotherapy treatment comprising the steps of:

using a machine capable of delivering a radiation beam for the treatment;

positioning a patient on a couch top, said couch top having a frame with side members, at least two movable support beams extending from said frame parallel to said side members of the frame in a longitudinal direction;

a horizontally extending fixed panel affixed to said frame over said two movable support beams for supporting said patient thereon and a horizontally extending removable panel disposed over said two movable support beams and adjacent to said fixed panel for also supporting said patient; and moving one of said movable support beams in a direction perpendicular to said longitudinal direction over linear slide bearing ways to avoid attenuation of said radiation beam used in the treatment while leaving the other of said movable support beams in place.

* * * * *